United States Patent [19]
Abrevaya et al.

[11] Patent Number: 6,015,933
[45] Date of Patent: Jan. 18, 2000

[54] PROCESS FOR REMOVING POLYMERIC BY-PRODUCTS FROM ACETYLENE HYDROGENATION PRODUCT

[75] Inventors: Hayim Abrevaya, Wilmette; Bipin V. Vora, Darien, both of Ill.

[73] Assignee: UOP LLC, Des Plaines, Ill.

[21] Appl. No.: 09/115,481

[22] Filed: Jul. 15, 1998

[51] Int. Cl.$^7$ .............................. C07C 7/00; C07O 7/10
[52] U.S. Cl. ..................... 585/810; 585/264; 585/802; 585/809; 585/833
[58] Field of Search .................... 585/802, 810, 585/809, 833, 264

[56] References Cited

U.S. PATENT DOCUMENTS

| | | | |
|---|---|---|---|
| 3,342,891 | 9/1967 | Poons et al. | 260/681.5 |
| 3,541,178 | 11/1970 | Nettesheim | 260/681.5 |
| 3,842,137 | 10/1974 | Libers et al. | 260/681.5 R |
| 3,898,298 | 8/1975 | Desiderio et al. | 260/681.5 |
| 4,277,313 | 7/1981 | Mehra et al. | 203/32 |
| 4,469,907 | 9/1984 | Araki et al. | 585/259 |
| 4,704,492 | 11/1987 | Nemet-Mavrodin | 585/259 |
| 5,304,699 | 4/1994 | Jenkins et al | 585/810 |
| 5,414,170 | 5/1995 | McCue et al. | 585/264 |

FOREIGN PATENT DOCUMENTS 2 040 995   10/1982   United Kingdom ............ C07C 7/167

OTHER PUBLICATIONS

Sarkany, A; Weiss, A.H.; Szilagyi, T.; Sandor, P.; Guczi, L. *Applied Catalysis* 1984, 12, 373, 379.

Abrevaya, H.; Vora, B.V. Lentz, R.A.; "Improved Butadiene Technology for Naphtha Cracking," Presented at the Fifth World Congress of Chemical Engineerinig, San Diego, Jul. 1996.

*Primary Examiner*—Walter D. Griffin
*Assistant Examiner*—Tam M. Nguyen
*Attorney, Agent, or Firm*—Thomas K. McBride; Frank S. Molinaro; Maryann Maas

[57] ABSTRACT

A process to remove polymeric by-products from the product of an acetylene selective hydrogenation reactor has been developed. The product is generated by introducing hydrogen and a liquid hydrocarbon stream containing largely butadiene and some acetylenes to a reactor containing a catalyst effective for the selective hydrogenation of acetylenes. The product contains at least hydrogen, butadiene, and polymeric by-products. The pressure of the product is reduced and the product cooled. The cooled product is conducted to a low pressure flash drum to produce a hydrogen enriched stream and a butadiene and polymeric by-product-enriched stream. The hydrogen-enriched stream is removed. The butadiene and polymeric by-product is passed to a knockout drum to produce a stream enriched in butadiene and polymeric by-products having less than about 12 carbon atoms and a stream enriched in polymeric by-products having about 12 or more carbon atoms. The stream enriched in polymeric by-products having about 12 or more carbon atoms is removed from the process. Polymeric by-products containing less than about 12 carbon atoms may be removed from the remaining stream by conducting a solvent and the stream enriched in butadiene and polymeric by-products containing less than about 12 carbon atoms to an extractive distillation column. In the extractive distillation column, the butadiene and polymeric by-products containing less than about 12 carbon atoms are carried with the solvent and removed in a bottoms stream as an extract mixture while the butanes and butenes are removed in an extractive distillation overhead stream. The bottoms extract stream is conducted to a stripper column where the solvent and the polymeric by-products are separated from the butadiene.

12 Claims, 1 Drawing Sheet

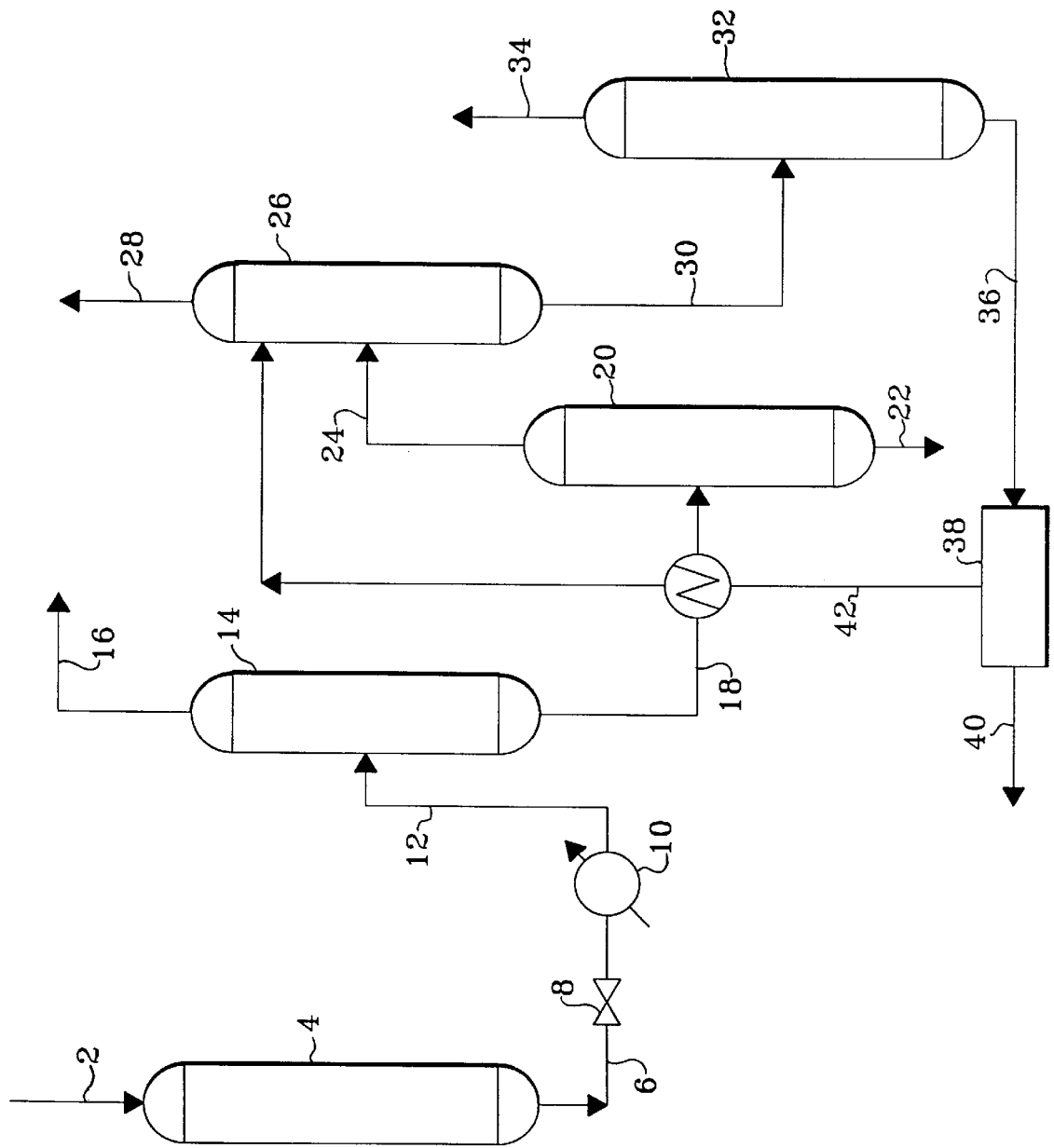

PROCESS FOR REMOVING POLYMERIC BY-PRODUCTS FROM ACETYLENE HYDROGENATION PRODUCT

BACKGROUND OF THE INVENTION

Butadiene is an important starting material for the production of high molecular weight polymers and is used extensively to form synthetic rubber including styrene-butadiene rubber, nitrile-butadiene rubber, buna-S rubber, and trans-polybutadiene rubber, and adiponitrile and styrene butadiene latex in paints. Butadiene is usually a by-product from steam cracking naphtha. However, the product butadiene regularly contains impurities that must be removed before the butadiene may be used as a starting material. The principal impurities are acetylenes including ethylacetylene, methylacetylene and vinylacetylene. Historically, two approaches have been used to remove the acetylenes: extractive distillation using a solvent to selectively absorb the acetylenes, or selective hydrogenation of the acetylenes. Examples of selective hydrogenation include U.S. Pat. Nos. 3,342,891, 3,541,178, 3,842,137, 3,898,298, 4,277,313, 4,469,907, 4,704,492, 5,414,170, and GB 2 040 995.

The patents U.S. Pat. Nos. 3,541,178, 3,842,137, 4,469,907, and U.S. Pat. No. 4,704,492 provide alternate methods of introducing hydrogen to the selective hydrogenation reactor. U.S. Pat. No. 3,342,891 teaches a process of fractionating the butadiene-containing stream into two portions with one portion enriched in acetylenes. Only that portion enriched in acetylenes is subjected to the selective hydrogenation. After selective hydrogenation the two portions are recombined. U.S. Pat. No. 5,414,170 discloses a process for selectively hydrogenating the acetylenes in an olefin plant process stream downstream of a front end depropanizer and upstream of further separation zones. U.S. Pat. No. 3,898,298 discloses selective hydrogenation of vinylacetylene using palladium on alumina catalysts at 35° C. and 7 atmospheres to achieve mixed phase operation. GB 2 040 995 discloses admixing a recycle stream and a fresh $C_4$ stream and hydrogenating the mixture, fractionating the product, feeding back an acetylenic stream and recovering butadiene. U.S. Pat. No. 4,277,313 discloses first selectively hydrogenating $C_4$-alkyne components and then using extractive distillation to separate a 1,3-butadiene-rich selective solvent extract phase.

As shown in the above references, the selective hydrogenation of acetylenes is generally performed using a catalytic composite. However, a drawback of catalytic hydrogenation is that some of the acetylenes will form polymeric by-products having from about 8 to about 36 carbon atoms; see Sarkany, A.; Weiss, A. H.; Szilagyi, T.; Sandor P.; Guczi L. *Applied Catalysis* 1984, 12, 373–379. These polymeric by-products must be removed before the butadiene can be successfully used as a starting material. One technique of removing the polymeric by-products is to distill the reactor effluent; see Abrevaya, H; Vora, B. V; Lentz, R. A., "Improved Butadiene Technology for Naphtha Cracking," Presented at the Fifth World Congress of Chemical Engineering, San Diego, July 1996. The present invention provides a process for the removal of polymeric by-products from an acetylene selective hydrogenation reactor product by employing low capital cost and low maintenance equipment and thereby reducing the overall cost of the process as compared to other selective hydrogenation processes. Specifically, the present invention eliminates the need for an expensive distillation column to remove polymeric by-products by using a cost efficient combination of a cooler, a low pressure flash drum, and a knockout drum.

SUMMARY OF THE INVENTION

The purpose of the invention is to remove polymeric by-products from the product of a process for selectively hydrogenating acetylenes in a liquid hydrocarbon stream containing largely butadiene. Acetylenes in the liquid hydrocarbon stream are selectively hydrogenated in a reactor to produce a reactor product containing at least hydrogen, butadiene and polymeric by-products having from about 8 to about 36 carbon atoms, and typically further containing butenes and butanes. At least a portion of the hydrogen from the reactor product is removed in a low pressure flash drum. Polymeric by-products having about 12 or more carbon atoms are separated and removed from the low pressure flash drum effluent by phase separation to produce an overhead stream containing at least butadiene and polymeric by-products having less than about 12 carbon atoms and a bottoms stream containing polymeric by-products having about 12 or more carbon atoms. Polymeric by-products having less than about 12 carbon atoms are separated and removed from the overhead stream by extractive distillation. The extractive distillation may be concurrently performed in an existing extractive distillation unit for the separation of acetylene-free butadiene from butanes and butenes.

BRIEF DESCRIPTION OF THE DRAWING

The FIGURE is a schematic representation of the separation process of the present invention. The drawing has been simplified by the deletion of a large number of pieces of apparatus customarily employed in processes of this nature which are not specifically required to illustrate the performance of the invention.

DETAILED DESCRIPTION OF THE INVENTION

In general terms, the invention is a cost-efficient process for removing undesired polymeric by-products containing about 12 or more carbon atoms from the product of a selective hydrogenation reactor that is used to selectively hydrogenate acetylenes in a liquid hydrocarbon stream containing largely butadiene. Polymeric by-products containing less than about 12 carbon atoms may be removed through integration of the invention with a butadiene extraction process. The goals of the invention are accomplished without significant loss of butadiene.

Processes for the selective hydrogenation of acetylenes in a liquid hydrocarbon stream containing largely butadiene are known, and the product of any such known process that generates polymeric by-products may be treated for the removal of the polymeric by-products using the present invention. For ease of understanding, the description below outlines a particular selective hydrogenation process. However, as stated earlier, the present invention may be applied to treat the product of any known acetylene selective hydrogenation process that generates polymeric by-products.

The feed to a selective hydrogenation reactor is typically a crude $C_4$ stream containing butadiene, butenes, butanes, and acetylenes. Some small amount of lighter components may also be present. The crude $C_4$ stream may be produced from a variety of sources with the most common being the steam cracking of naptha. The general term "butadiene" is meant to include both 1,2-butadiene and 1,3-butadiene, and the butadiene typically makes up from about 35 to about 50 weight percent of the crude $C_4$ feed stream. The butenes are usually present as a mixture of 1-butene and 2-butene, and the butanes are a mixture of normal butane and isobutane. The butenes and butanes together make up from about 40 to 50 weight percent of the crude $C_4$ feed stream. The acetylenes include vinylacetylene, ethylacetylene, and methylacetylene and are frequently from about 0.5 to about 1.5 weight percent of the crude $C_4$ feed stream, but can be as high as 3 weight percent of the crude $C_4$ feed stream. Of the acetylenes, a large portion, usually 75 weight percent, is vinylacetylene.

Hydrogen, either pure or as a mixture with inert compound(s), and the feed stream are introduced to a reactor for the selective hydrogenation of the acetylenes. The reactor is a fixed bed type reactor containing a catalytic composite effective for the selective hydrogenation of the acetylenes. Such catalytic composites are known and include composites having copper, one or more Group VIII metals, or a mixture thereof, with a refractory inorganic oxide carrier material. Other activator metals may also be present. Suitable catalysts include those disclosed in U.S. Pat. Nos. 3,651,167, 3,912,789, 4,493,906, 4,440,956, 3,751,508 and others. The most preferred catalyst is a composite having copper, nickel, manganese, and cobalt dispersed on a gamma alumina support with a surface area of from about 150 to about 250 $m^2/g$. The reactor may be a single bed reactor or a series of interconnected sub-beds. The reactor may be operated in a swing bed mode, where one sub-bed is on-line and the other sub-bed is off-line being regenerated, or is fully regenerated and on standby. The reactor is operated at a temperature ranging from about 32° C. (90° F) to about 82° C. (180° F.) and a pressure ranging from about 2,068 kPa (300 psia) to about 3,103 kPa (450 psia), and the components in the reactor are in the liquid phase.

As hydrogen and the crude $C_4$ feed stream contact the catalytic composite in the reactor, the vinylacetylene is hydrogenated to 1,3-butadiene, the ethylacetylene is hydrogenated to 1-butene, and the methylacetylene is hydrogenated to propylene. The catalytic composite is chosen so that the acetylenes are selectively hydrogenated, and only minimal, if any, butadiene is hydrogenated. The butadiene and acetylenes, however, also have a tendency to polymerize and form heavy hydrocarbon by-products containing from about 8 up to about 36 carbon atoms. A portion of the polymeric by-products remains with the catalyst and a portion of the polymeric by-products is removed from the reactor in the reactor product. Therefore, the reactor product contains hydrogen, butadiene, butenes, butanes, polymeric by-products, and a small amount of lighter components such as propane and propylene.

The reactor product exits the reactor at the operating pressure and temperature of the reactor, which, in the above particular case, are preferably close to 2,568 kPa (375 psia) and close to 74° C. (165° F.). The pressure is then lowered to a range of from about 413 kPa (60 psia) to about 620 kPa (90 psia) and the temperature is cooled to a range of from about 4° C. (40° F.) to about 21° C. (70° F.), with the preferred conditions being about 620 kPa (90 psia) and about 10° C. (50° F.). The pressure and temperature may be lowered using any conventional means such as pressure control valves and heat exchange with chilled water. It is most preferred to first cool the product to about 38° C. (100° F.) using ambient cooling water, then to separate the liquid product from that portion that is still vapor, and finally cool only the vapor to 10° C. (50° F.) to form additional liquid which is combined with the liquid product. Once the pressure and temperature are lowered, the product is introduced to a low pressure flash drum. The low pressure flash drum is operated at a pressure ranging from about 413 kPa (60 psia) to about 620 kPa (90 psia) and a temperature ranging from about 4° C. (40° F.) to about 21° C. (70° F.). Within the low pressure flash drum hydrogen evolves as a vapor phase and the hydrocarbons settle into a liquid phase. The hydrogen is removed in an overhead vapor stream, and the hydrocarbons are removed in a bottoms liquid stream. Typically, from about 60 to about 90 percent of the available hydrogen is removed in the low pressure flash drum overhead stream, thereby leaving from about 10 to about 40 percent of the available hydrogen in the low pressure flash drum bottoms liquid stream. The hydrogen may be recycled to the reactor which has the added benefit of recovering any accompanying butadiene. However, when the low pressure flash drum overhead stream is recycled to the reactor, a small amount of purge needs to be maintained to prevent accumulation of light components such as propane and propylene. Alternatively, the low pressure flash drum overhead stream containing the hydrogen may be flared.

The bottoms liquid stream is heated to a temperature ranging from about 49° C. (120° F.) to about 71° C. (160° F.) and preferably about 54° C. (130° F.) using commonly known means such as heat exchange. Preferably, the bottoms liquid stream is heat exchanged with hot solvent from a butadiene solvent purification system. Typically the heat exchange causes vaporization of most of the bottoms liquid stream, leaving most of the heavy polymers in a liquid phase. The heated stream is introduced to a knockout drum operated at a pressure ranging from about 413 kPa (60 psia) to about 827 kPa (120 psia) and a temperature ranging from about 49° C. (120° F.) to about 71° C. (160° F.). The preferred operating pressure of the knockout drum is 620 kPa (90 psia) and the preferred temperature is 54° C. (130° F.). At the specified operating conditions, the lighter boiling materials in the liquid bottoms stream including butadiene, butenes, butanes, and lighter hydrocarbons are in a vapor phase and easily phase separated from the polymeric by-products that contain about 12 or more carbon atoms that remain as a liquid. Liquid polymeric by-products having 12 or more carbon atoms are then removed and collected. The vapor components are removed in a knockout drum overhead stream and contain less than 5 weight percent of polymeric by-products having about 12 or more carbon atoms.

Some polymeric by-products having less than about 12 carbon atoms may still be contained in the knockout drum overhead stream. For example, vinylcyclohexene would be a polymeric by-product that would be carried in the knockout drum overhead stream. These polymeric by-products may be removed through integration with a traditional butadiene extractive distillation system. The extractive distillation system begins with an extractive distillation column operated at pressures ranging from about 517 kPa (75 psia) to about 861 kPa (125 psia) and temperatures ranging from about 38° C. (100° F.) to about 121° C. (250° F.). A solvent such as dimethylacetamide, dimethylformamide, furfural, N-methyl pyrrolidone, formylmorpholine, and acetonitrile, is typically introduced as an extractant vapor near the top of the column. The less soluble butenes, butanes, propane and propylene are removed in the extractive distillation column overhead stream, and the more soluble butadiene and polymeric by-products are carried with the solvent and removed as a mixture with the solvent in the extractive distillation column bottoms stream. A small amount of soluble hydrogen can be removed as an overhead net gas stream from an overhead condenser of the extractive distillation column.

The extractive distillation column bottoms stream is conducted to a butadiene stripping column operated at pressures ranging from about 103 kPa (15 psia) to about 241 kPa (35 psia) and temperatures ranging from about 38° C. (100° F.) to about 177° C. (350° F.). In this column the solvent is separated from the butadiene. The butadiene is removed in a stripping column overhead stream and the polymeric by-products having less than about 12 carbon atoms will be carried with the solvent and removed in a stripping column bottoms stream. The stripping column overhead stream contains at least 99 weight percent butadiene with small amounts of butanes and butenes and no more than about 5 parts per million polymeric by-products. This stream may be processed further to separate the butadiene isomers for use as a starting material in processes such as the production of synthetic rubber or adiponitrile and styrenebutadiene latex for paint. The stripping column bottoms stream may be conducted to an existing solvent purification unit where impurities including the polymeric by-products are removed from the solvent before the solvent is recycled to the extractive distillation column.

Without intending any limitation on the scope of the present invention and as merely illustrative, this invention is explained below in specific terms as applied to a particular embodiment of the invention. For ease of understanding, a specific acetylene selective hydrogenation process is detailed, but other acetylene selective hydrogenation processes may be used. Turning now to the FIGURE, a crude $C_4$ stream, as described above, and hydrogen are conducted in line 2 to a selective hydrogenation reactor 4 operating at 2,517 kPa (365 psia) and 73° C. (163° F.) at the exit. Reactor 4 contains a fixed bed of catalytic composite having copper, nickel, manganese, and cobalt dispersed on a gamma alumina support having a surface area of from about 150 to about 250 $m^2/g$. In reactor 4, acetylenes are selectively hydrogenated and polymeric by-products are produced. Reactor product in line 6 contains hydrogen, butanes, butenes, butadiene, and polymeric by-products, and the product is at the operating conditions of the reactor. Pressure valve 8 reduces the pressure of the reactor product and ambient cooling water/chilled water heat exchanger 10 cools the temperature of the reactor product so that the reactor product now in line 12 is at 606 kPa,(88 psia) and 10° C. (50° F.). Reactor product in line 12 is introduced to low pressure flash drum 14 operating at 606 kPa (88 psia) and 10° C. (50° F.). In low pressure flash drum 14, 60 weight percent of the hydrogen contained in the reactor product is evolved and removed in line 16. The hydrogen in line 16 may be recycled to reactor 4 or may be passed to another process. The hydrogen-reduced product is removed from low pressure flash drum 14 in line 18.

The hydrogen reduced product in line 18 is heated to 55° C. (131° F.) by heat exchange with hot solvent in line 42 (discussed below) and introduced to knockout drum 20 operating at 593 kPa (86 psia) and 55° C. (131° F.). Polymeric by-products having about 12 or more carbon atoms are removed from the bottom of knockout drum 20 in line 22 and a knockout drum overhead which is reduced in polymeric by-products having about 12 or more carbon atoms is removed from knockout drum 20 in line 24. Knock out drum overhead is conducted in line 24 to extractive distillation column 26. Extractive distillation column 26 is operated at 579 kPa (84 psia) with a receiver temperature of 38° C. (100° F.). Dimethylformamide heated to 60° C. (140° F.) or another appropriate solvent is also introduced to extractive distillation column 26 as the extractant. The solvent extracts the butadiene and the polymeric by-products and the extract mixture is removed from the bottom of extractive distillation column 26 in line 30. The nonextracted components including hydrogen, butanes, and butenes are removed from extractive distillation column 26 in overhead stream 28. The extract mixture in line 30 is introduced to low pressure stripping column 32 operating at 103 kPa (15 psia) and 38° C. (100° F.) as measured at the overhead. Butadiene is separated from the extract mixture and removed from low pressure stripping column 32 in line 34. The butadiene may be processed further to separate individual isomers (not shown). Solvent and polymeric by-products having less than about 12 carbon atoms are removed from low pressure stripping column 32 in line 36 and are conducted to a solvent purification unit 38 where polymeric by-products are separated and removed in line 40, and solvent is removed in line 42. The solvent in line 42 is recycled to extractive distillation column 26.

A simulation based on the above specific embodiment was performed using Hysym simulation software available from Hyprotech Ltd. The simulation resulted in the material balance shown in the table below. All values listed in the table have units of kg/hr. Note that substantially all of the polymeric by-products having about 12 or more carbon atoms are removed from the process via stream 22, and that substantially all of the polymeric by-products having less than about 12 carbon atoms are removed from the process via line 40.

TABLE

| | Stream Number as Shown in FIG. | | | | | | | | | |
|---|---|---|---|---|---|---|---|---|---|---|
| | 6 | 16 | 18 | 22 | 24 | 28 | 30 | 34 | 36 | 40 |
| Hydrogen | 6 | 3.6 | 3 | — | 3 | 3 | — | — | — | — |
| Propane | 25 | <1 | 25 | <1 | 25 | 25 | — | — | — | — |
| Propylene | 109 | 1 | 108 | <1 | 108 | 108 | — | — | — | — |
| Butanes | 1894 | 3 | 1891 | 10 | 1880 | 1880 | — | — | — | — |
| Butenes | 12,836 | 22 | 12,815 | 69 | 12,746 | 12,627 | 119 | 119 | — | — |
| Butadienes | 11,185 | 19 | 11,166 | 59 | 11,108 | 55 | 11,053 | 11,053 | — | — |
| Isopentane | 62 | — | 62 | <1 | 62 | — | 62 | 62 | — | — |
| Vinylcyclohexene | 21 | — | 30 | 6 | 24 | — | 24 | — | 24 | 24 |
| Polymeric By-products Having 12 or More Carbon Atoms | 73 | — | 73 | 71 | 2 | — | 2 | — | 2 | — |

It must be emphasized that the above description is merely illustrative of a preferred embodiment and is not intended as an undue limitation on the generally broad scope of the invention. Moreover, while the description is narrow in scope, one skilled in the art would understand how to extrapolate to the broader scope of the invention. For example, the operation at different conditions can be readily extrapolated from the foregoing description.

What is claimed is:

1. A process for removing polymeric by-products from the product of the selective hydrogenation of acetylenes in a liquid stream containing largely butadiene, said product containing at least hydrogen, butadiene, and polymeric by-products having from about 8 to about 36 carbon atoms; said process comprising:

a) removing at least a portion of the hydrogen from the product in a low pressure flash drum to provide a low pressure flash drum effluent;

b) separating and removing polymeric by-products having about 12 or more carbon atoms from the low pressure flash drum effluent by phase separation to produce an overhead stream containing at least butadiene and polymeric by-products having less than about 12 carbon atoms and a bottoms stream containing polymeric by-products having about 12 or more carbon atoms; and c) separating and removing polymeric by-products having less than about 12 carbon atoms from the overhead stream by extractive distillation.

2. The process of claim 1 wherein the low pressure flash drum is operated at a pressure in the range of about 414 kPa (60 psia) to about 620 kPa (90 psia) and a temperature in the range of from about 4° C. (40° F.) to about 21° C. (70° F.).

3. The process of claim 1 wherein the phase separation is conducted at a pressure in the range of about 414 kPa (60 psia) to about 827 kPa (120 psia) and a temperature in the range of about 49° C. (120° F.) to about 71° C. (160° F.).

4. The process of claim 1 wherein the extractive distillation is conducted at a pressure of from about 517 kPa (75 psia) to about 862 kPa (125 psia) and a temperature of from about 38° C. (100F.) to about 121° C. (250° F.).

5. A process for removing polymeric by-products containing 12 or more carbon atoms in a product arising from the selective hydrogenation of acetylenes in a liquid stream containing largely butadiene, said product containing at least hydrogen, butadiene, and polymeric by-products having from about 8 to about 36 carbon atoms; said process comprising:

a) passing the product to a low pressure flash drum operating at a pressure in the range of about 414 kPa (60 psia) to about 620 kPa (90 psia) and a temperature in the range of from about 4° C. (40° F.) to about 21° C. (70° F.) to produce a hydrogen-enriched stream and a butadiene and polymeric by-product-enriched stream;

b) passing the butadiene and polymeric by-product-enriched stream to a knockout drum operating at a pressure in the range of about 414 kPa (60 psia) to about 827 kPa (120 psia) and a temperature in the range of about 49° C. (120° F.) to about 71° C. (160° F.) for phase separation to produce a stream enriched in butadiene and polymeric by-products having less than about 12 carbon atoms and a stream enriched in polymeric by-products having about 12 or more carbon atoms; and c) removing the stream enriched in polymeric by-products having about 12 or more carbon atoms.

6. The process of claim 5 further comprising recycling the hydrogen-enriched stream to a reactor for selective hydrogenation of acetylenes in a liquid stream containing largely butadiene.

7. The process of claim 5 wherein the pressure of the low pressure flash drum is about 620 kPa (90 psia) and the temperature of the low pressure flash drum is about 10° C. (50° F.).

8. The process of claim 5 wherein the pressure of the knockout drum is about 620 kPa (90 psia) and the temperature of the knockout drum is about 54° C. (130° F.).

9. The process of claim 5 further comprising:

a) introducing a solvent in the vapor phase and the stream enriched in butadiene and polymeric by-products having less than about 12 carbon atoms to an extractive distillation column operating at a pressure of from about 517 kPa (75 psia) to about 862 kPa (125 psia) and a temperature of from about 38° C. (100° F.) to about 121° C. (250° F.) to produce a second stream enriched in hydrogen and a stream enriched in solvent, butadiene, and polymeric by-products having less than about 12 carbon atoms;

b) passing the stream enriched in solvent, butadiene, and polymeric by-products having less than about 12 carbon atoms to a butadiene stripper column operating at a pressure of from about 103 kPa (15 psia) to about 241 kPa (35 psia) and a temperature of from about 38° C. (100° F.) to about 177° C. (350° F.) to produce a stream enriched in butadiene and a stream enriched in solvent and polymeric by-products having less than about 12 carbon atoms; and c) removing the stream enriched in solvent and polymeric by-products having less than about 12 carbon atoms.

10. The process of claim 9 wherein the solvent is selected from the group consisting of dimethylacetamide, dimethylformamide, furfural, N-methyl pyrrolidone, formylmorpholine, and acetonitrile.

11. The process of claim 9 further comprising passing the stream enriched in solvent and polymeric by-products having less than about 12 carbon atoms to a solvent purification unit to produce a stream enriched in polymeric by-products having less than about 12 carbon atoms and a stream enriched in solvent.

12. The process of claim 11 further comprising recycling the stream enriched in solvent to the extractive distillation column.

\* \* \* \* \*